United States Patent [19]

Negi et al.

[11] 4,448,775
[45] May 15, 1984

[54] 3-CARBAMOYLOXYMETHYLCEPHEM DERIVATIVES, AND ANTIBACTERIAL DRUGS CONTAINING SAME

[75] Inventors: Shigeto Negi, Tokyo; Yoshimasa Machida; Hiroshi Yamauchi, both of Ibaraki; Isao Saito, Tokyo; Yoshikazu Hasagawa; Tamio Kawamura, both of Gifu, all of Japan

[73] Assignee: Eisai Co., Ltd., Tokyo, Japan

[21] Appl. No.: 422,440

[22] Filed: Sep. 23, 1982

[30] Foreign Application Priority Data

Sep. 29, 1981 [JP]  Japan ................. 56-153009

[51] Int. Cl.³ ............... A61K 31/545; C07D 501/34; C07D 501/57
[52] U.S. Cl. .................... 424/246; 544/21; 544/22
[58] Field of Search ............ 424/246; 544/21, 22

[56] References Cited

U.S. PATENT DOCUMENTS

| | | | |
|---|---|---|---|
| 4,138,554 | 2/1979 | Naito et al. | 544/22 |
| 4,172,198 | 10/1979 | Kamiya et al. | 544/22 |
| 4,285,939 | 8/1981 | Machida et al. | 544/28 |
| 4,285,940 | 8/1981 | Machida et al. | 544/28 |
| 4,344,944 | 8/1982 | Machida et al. | 544/21 |

Primary Examiner—Paul M. Coughlan, Jr.
Attorney, Agent, or Firm—Wenderoth, Lind & Ponack

[57] ABSTRACT

The invention provides 3-carbamoyloxymethylcephem derivatives represented by the general formula:

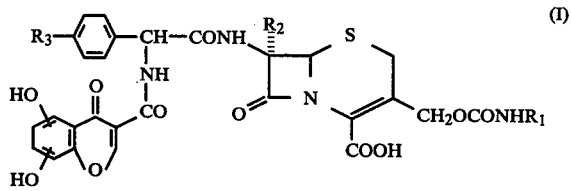

wherein $R_1$ represents hydrogen atom or trichloroacetyl group, $R_2$ represents hydrogen atom or methoxy group, and $R_3$ represents hydrogen atom or hydroxyl group, or pharmaceutically acceptable salt thereof. The cephem derivatives of the invention are useful as antibacterial drugs.

5 Claims, No Drawings

3-CARBAMOYLOXYMETHYLCEPHEM DERIVATIVES, AND ANTIBACTERIAL DRUGS CONTAINING SAME

The present invention relates to the field of antibacterially active cephalosporin derivatives. In particular, it relates to novel 3-carbamoyloxymethylcephem derivatives represented by the general formula (I):

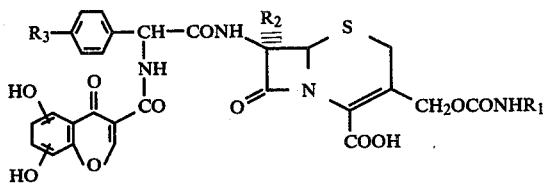

(I)

wherein $R_1$ represents a hydrogen atom or a trichloroacetyl group, $R_2$ represents a hydrogen atom or a methoxy group, and $R_3$ represents a hydrogen atom or a hydroxyl group.

The compounds according to this invention have a broad antibacterial spectrum and are effective particularly against gram-negative bacteria such as *Pseudomonas aeruginosa*, *Klebsiella pneumoniae* and the like.

The compounds of this invention may be synthetically prepared by the following described processes.

A compound of the above general formula (I), may be obtained by reacting a compound represented by the general formula (II):

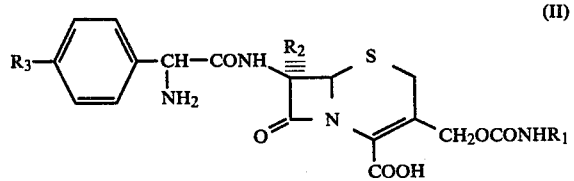

(II)

wherein $R_1$, $R_2$ and $R_3$ have the same significance as defined above or a salt thereof with a compound represented by the general formula (III):

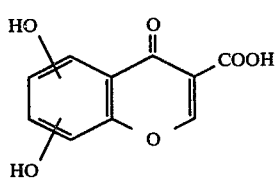

(III)

or a reactive derivative thereof.

In the above process, it is preferred to carry out the reaction in the presence of a condensing agent such as for example N,N'-dicyclohexylcarbodiimide, N,N'-diethylcarbodiimide, N-cyclohexyl-N'-(2-morpholinoethyl)carbodiimide, ethyl phosphite, phosphorus oxychloride or oxalyl chloride when the compound of the general formula (III) which is a carboxylic acid, and thus contains a carboxyl group, is used. On the other hand, a relative derivative of the compound of the general formula (III) in which derivative a substituent group is coupled to the carboxyl group may be used. The reactive derivative may for example be an acid halide such as an acid chloride or acid bromide; a symmetric acid anhydride; a mixed acid anhydride with a carboxylic acid such as chloroformic acid, trimethyl acetic acid or diphenylacetic acid; an activated ester of 2-mercaptopyridine, cyanomethanol, p-nitrophenol, 2,4-dinitrophenol or pentachlorophenol; an activated acid amide such as N-acylsaccharin or N-acylphthalimide; or the like.

As a salt of the compound of the general formula (II) there may be mentioned for example for trifluoroacetate, hydrochloride, or methanesulfonate, and the like.

The above reaction may be carried out in an inert solvent in the presence or the absence of a basic reagent or silylating agent, at a temperature of from $-50°$ C. to $50°$ C., and preferably $-20°$ C. to $30°$ C.

As exemplary inert solvents there may be mentioned acetone, tetrahydrofuran, dimethylacetamide, dimethylformamide, dioxane, dichloromethane, chloroform, benzene, toluene, ethyl acetate and mixtures thereof.

Illustrative basic reagents include alkali metal hydroxides such as sodium hydroxide and potassium hydroxide; alkali metal hydrogencarbonates such as sodium hydrogencarbonate and potassium hydrogencarbonate; and amines such as triethylamine, pyridine, dimethylaniline and N-methylmorpholine.

It is feasible to employ as the silylating agent, for example, N,O-bis(trimethylsilyl)acetamide, hexamethyldisilazane, trimethylsilylacetamide or the like.

Among the compounds represented by the general formula (I), those containing a hydrogen atom as $R_1$ may also be synthesized in accordance with the following described process.

A compound represented by the general formula (V):

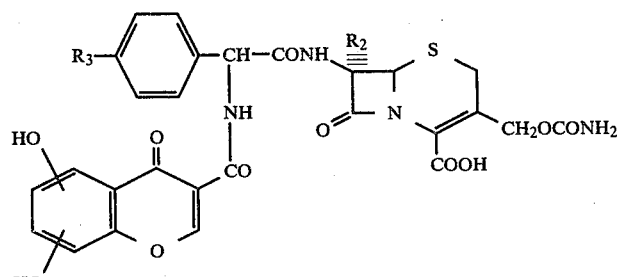

(V)

wherein $R_2$ and $R_3$ have the same significance as defined above may be obtained by reacting a compound represented by the general formula (IV):

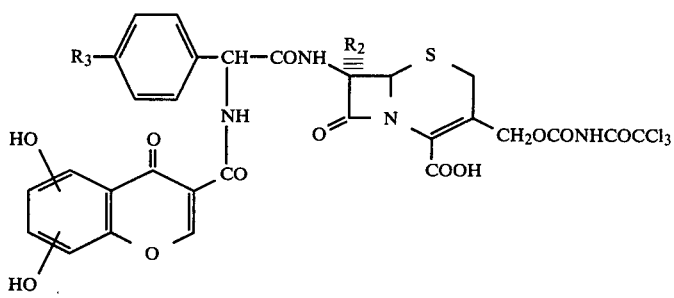

(IV)

wherein $R_2$ and $R_3$ have the same significance as defined above with a base.

The above reaction may be carried out at 0° C.–50° C. in water or a mixed solvent of water and a hydrophilic solvent. As such a hydrophilic solvent, may be mentioned for example ethanol, methanol, propanol, tetrahydrofuran, acetone, acetonitrile or dimethylformamide.

On the other hand, exemplary bases useful in the practice of the above reaction include, for example, alkali metal hydrogencarbonates such as sodium hydrogencarbonate and potassium hydrogencarbonate; alkali metal carbonates such as sodium carbonate and potassium carbonate; and alkali metal hydroxides such as sodium hydroxide and potassium hydroxide.

As pharmaceutically acceptable salts of the compound of the general formula (I) there may be mentioned for example the sodium, potassium, calcium, ammonium, triethylamine, dicyclohexylamine and procaine salts. These salts may be obtained from the compound of the general formula (I) in accordance with any salt-forming reaction which per se is commonly known in the art.

As specific compounds according to this invention, the following compounds and their sodium salts may be mentioned:

7β-[D-2-(6,7-Dihydroxychromon-3-carboxamido)-2-(4-hydroxyphenyl)acetamido]-3-trichloroacetylcarbamoyloxymethyl-3-cephem-4-carboxylic acid;

7β-[D-2-(6,7-Dihydroxychromon-3-carboxamido)-2-(4-hydroxyphenyl)acetamido]-7α-methoxy-3-trichloroacetylcarbamoyloxymethyl-3-cephem-4-carboxylic acid;

7β-[D-2-(6,7-Dihydroxychromon-3-carboxamido)-2-phenylacetamido]-3-trichloroacetylcarbamoyloxymethyl-3-cephem-4-carboxylic acid;

7β-[D-2-(7,8-Dihydroxychromon-3-carboxamido)-2-(4-hydroxyphenyl)acetamido]-3-trichloroacetylcarbamoyloxymethyl-3-cephem-4-carboxylic acid;

7β-[D-2-(7,8-Dihydroxychromon-3-carboxamido)-2-(4-hydroxyphenyl)acetamido]-7α-methoxy-3-trichloroacetylcarbamoyloxymethyl-3-cephem-4-carboxylic acid;

7β-[D-2-(6,7-Dihydroxychromon-3-carboxamido)-2-(4-hydroxyphenyl)acetamido]-3-carbamoyloxymethyl-3-cephem-4-carboxylic acid;

7β-[D-2-(6,7-Dihydroxychromon-3-carboxamido)-2-phenylacetamido]-3-carbamoyloxymethyl-3-cephem-4-carboxylic acid;

7β-[D-2-(6,7-Dihydroxychromon-3-carboxamido)-2-(4-hydroxyphenyl)acetamido]-7α-methoxy-3-carbamoyloxymethyl-3-cephem-4-carboxylic acid;

7β-[D-2-(6,7-Dihydroxychromon-3-carboxamido)-2-phenylacetamido]-7α-methoxy-3-carbamoyloxymethyl-3-cephem-4-carboxylic acid;

7β-[D-2-(7,8-Dihydroxychromon-3-carboxamido)-2-(4-hydroxyphenyl)acetamido]-3-carbamoyloxymethyl-3-cephem-4-carboxylic acid;

7β-[D-2-(7,8-Dihydroxychromon-3-carboxamido)-2-phenylacetamido]-3-carbamoyloxymethyl-3-cephem-4-carboxylic acid; and 7β-[D-2-(7,8-Dihydroxychromon-3-carboxamido)-2-(4-hydroxyphenyl)acetamido]-7α-methoxy-3-carbamoyloxymethyl-3-cephem-4-carboxylic acid.

The compounds of this invention exhibit antibacterial activity, and are effective against the Gram-positive bacteria and the Gram-negative bacteria. Particularly, the compounds of this invention are effective against bacteria such as *Pseudomonas aeruginosa, Klebsiella pneumoniae* and the like that cause difficultly curable infections.

The dose of the compound of this invention, when used as anti-bacterial drugs, may range generally from 2 to 300 mg/kg/day, preferably from 10 to 100 mg/kg/day. This compound can be administered orally in the form of powder, granuel, tablet, capsule, syrup and the like, or parenterally in the form of injection, suppository, and the like.

These preparations to be employed can be provided by conventional processes. The preparations of powder, granule, tablet and capsule can be provided using appropriately excipients such as lactose, starch, white sugar, glucose, crystallized cellulose, and the like; disintegrants, such as, starch, calcium salt of carboxylmethylcellulose, calcium carbonate, dextrine, and the like; binders such as polyvinyl alcohol, ethylcellulose, gum arabic, tragacanth, hydroxypropylcellulose; and lubricants such as calcium stearate, magnesium stearate, talc and the like.

The preparations of syrup can be provided using appropriately sweetenings such as white sugar, sorbitol, glucose, fructose, and the like; dispersants and thickeners such as gum arabic, tragacanth, sodium salt of carboxymethylcellulose, methylcellulose, sodium arginate, and the like.

The preparations for injection can be provided using isotonic agents such as glucose, sodium chloride, sorbitol, and the like, and if required, suspending agents, surfactants, pH controlling agents or the like. Alternatively, the preparation for injection may be in the form of powder which can be dissolved prior to administration.

The suppository can be provided using a base such as cocao butter, polyethylene glycol, Witepsol (trademark Dynamite-Nobel-AG), and the like and, if required, a surfactant.

The following examples illustrate this invention, but are not to be construed as limiting the scope thereof.

EXAMPLE 1

7β-[D-2-(6,7-Dihydroxychromon-3-carboxamido)-2-(4-hydroxyphenyl)acetamido]-3-trichloroacetylcarbamoyloxymethyl-3-cephem-4-carboxylic acid 7β-[D-2-Amino-2-(4-hydroxyphenyl)acetamido]-3-trichloroacetylcarbamoyloxymethyl-3-cephem-carboxylic acid.trifluoroacetic acid (165 mg, i.e., 0.248 millimole) was suspended in ethyl acetate (20 ml), followed by an addition with stirring of N,O-bis(trimethylsilyl)acetamide (244 μl). The resulting mixture was stirred for an additional 20 minutes. 6,7-Dihydroxychromon-3-carbonylchloride (54 mg, i.e., 0.220 millimole) was further added. The thus-obtained mixture was stirred for 2 hours in an ice-water bath. It was then washed successively with 0.5-N hydrochloric acid (20 ml), water (3 times, each, 20 ml) and saturated saline (once, 20 ml). The thus-washed reaction mixture was dried over magnesium sulfate and the solvent was distilled off. The residue was added successively with acetone (1 ml), ether (50 ml) and n-hexane (50 ml). The resulting precipitate was collected through filtration to yield the desired product (130 mg) (yield: 71%).

IR spectrum(cm$^{-1}$, nujol): 1770, 1660, 1610.

NMR spectrum($\delta$, DMSO-d$_6$): 3.57(2H, br.s), 4.88(1H, d, J=14 Hz), 5.08(1H, d, J=4.5 Hz), 5.10(1H, d, J=14 Hz), 5.60–5.90(2H, m), 6.72(2H, d, J=8 Hz), 7.00(1H, s), 7.27(2H, d, J=8 Hz), 7.43(1H, s), 8.88(1H, s), 9.37(1H, d, J=10 Hz), 9.25(1H, s), 10.28(1H, d, J=8 Hz).

EXAMPLE 2

7β-[D-2-(6,7-Dihydroxychromon-3-carboxamido)-2-(4-hydroxyphenyl)acetamido]-3-carbamoyloxymethyl-3-cephem-4-carboxylic acid The compound obtained in Example 1 (50 mg, i.e., 0.068 millimole) was dissolved in a solvent mixture of methanol (4 ml) and tetrahydrofuran (2 ml). A 5% aqueous solution of sodium hydrogencarbonate (433 μl) was added. The resultant mixture was stirred for 2 hours. After distilling off the solvents under reduced pressure, the residue was extracted with ethyl acetate (20 ml) and 0.5-N hydrochloric acid (20 ml). The thus-obtained extract was washed with water (3 times, each, 20 ml) and then with saturated saline (once, 20 ml) and then dried over magnesium sulfate. The solvents were distilled off. To the residue, were successively added ethyl acetate (2 ml), ether (50 ml) and n-hexane (50 ml). The resultant precipitate was collected through filtration, leading to the provision of the intended product (21.2 mg) (yield: 50%).

IR spectrum(cm$^{-1}$, nujol): 1770, 1700, 1650, 1610.

NMR spectrum($\delta$, DMSO-d$_6$) 3.45(2H, br.s), 4.57(1H, d, J=13 Hz), 4.89(1H, d, J=13 Hz), 5.03(1H, d, J=4.5 Hz), 5.60–5.90(2H, m), 6.60(2H, br.s), 6.75(2H, d, J=8 Hz), 7.00(1H, s), 7.26(2H, d, J=8 Hz), 7.42(1H, s), 8.86(1H, s), 9.35(1H, d, J=10 Hz), 10.25(1H, d, J=8 Hz).

EXAMPLE 3

7β-[D-2-(6,7-Dihydroxychromon-3-carboxamido)-2-(4-hydroxyphenyl)acetamido]-7α-methoxy-3-trichloroacetylcarbamoyloxymethyl-3-cephem-4-carboxylic acid 7β-[D-2-Amino-2-(4-hydroxyphenyl)acetamido]-7α-methoxy-3-trichloroacetylcarbamoyloxymethyl-3-cephem-4-carboxylic acid.trifluoroacetic acid (170 mg, i.e., 0.245 millimole) was suspended in ethyl acetate (20 ml), to which N,O-bis(trimethylsilyl)acetamide 240 μl) was added. The resultant mixture was stirred for 20 minutes. Then, 6,7-dihydroxychromon-3-carbonylchloride (53 mg, i.e., 0.22 millimole) was added. The thus-obtained mixture was stirred for 2 hours. It was then successively washed with 0.5-N hydrochloric acid (20 ml), water (3 times, each, 20 ml), and saline (once, 20 ml). After drying the thus-washed mixture over magnesium sulfate, the solvents were distilled off. The residue was mixed successively with acetone (1 ml), ether (50 ml) and n-hexane (50 ml). The resulting precipitate was collected through filtration, thereby obtaining the intended product (148 mg) (yield: 79%).

IR spectrum(cm$^{-1}$, nujol): 1785, 1655, 1610.

NMR spectrum($\delta$, DMSO-d$_6$): 3.42(3H, s), 4.75–5.20(2H, m), 5.15(1H, s), 5.58–5.82(2H, m), 6.75(2H, d, J=8 Hz), 7.00(1H, s), 7.32(2H, d, J=8 Hz), 7.41(1H, s), 8.87(1H, s), 9.48(1H, s), 9.66(1H, s).

EXAMPLE 4

7β-[D-2-(6,7-Dihydroxychromon-3-carboxamido)-2-(4-hydroxyphenyl)acetamido]-7α-methoxy-3-carbamoyloxymethyl-3-cephem-4-carboxylic acid The compound obtained in Example 3 (50 mg, i.e., 0.065 millimole) was dissolved in methanol (4 ml) and then a 5% aqueous solution of sodium hydrogencarbonate (443 μl) was added. The resulting mixture was stirred for 2 hours. After causing the solvents to distill off under reduced pressures, the thus-obtained residue was extracted by adding ethyl acetate (20 ml) and 0.5-N hydrochloric acid (20 ml). The resultant extract was washed with water (3 times, each, 20 ml) and saline (once, 20 ml) and then dried over magnesium sulfate. The solvents were thereafter distilled off. The residue was then added successively with ethyl acetate (2 ml), ether (50 ml) and n-hexane (50 ml). The resulting precipitate was collected through filtration, thereby obtaining the intended product (347 mg) (yield: 81%).

IR spectrum(cm$^{-1}$, nujol); 1760, 1700, 1650, 1610.

NMR spectrum($\delta$, DMSO-d$_6$): 3.40(3H, s), 3.53(1H, d, J=12 Hz), 4.78(1H, d, J=12 Hz), 5.11(1H, s), 5.67(1H, d, J=8 Hz), 6.60(2H, s), 6.76(2H, d, J=8 Hz), 7.00(1H, s), 7.33(2H, d, J=8 Hz), 7.40(1H, s), 8.86(1H, s), 9.63(1H, s), 10.15(1H, d, J=8 Hz).

EXAMPLE 5

7β-[D-2-(6,7-Dihydroxychromon-3-carboxamido-2-phenylacetamido]-3-carbamoyloxymethyl-3-cephem-4-carboxylic acid 7β-(D-2-Amino-2-phenylacetamido)-3-carbamoyloxymethyl-3-cephem-4-carboxylic acid.trifluoroacetic acid (30 mg, i.e., 0.058 millimole) was suspended in ethyl acetate (20 ml). With stirring, N,O-bis(trimethylsilyl)acetamide (76 μl) was further added. The resulting mixture was stirred for an additional 20 minutes. Thereafter, 6,7-dihydroxychromon-3-carbonylchloride (13 mg, i.e., 0.054 millimole) was incorporated, followed by stirring the thus-formed mixture for 2 hours. It was then washed successively with 0.5-N hydrochloric acid (20 ml), water (3 times, each, 20 ml) and saturated saline (once, 20 ml). After drying the thus-washed mixture by adding magnesium sulfate, the solvents were distilled off. The residue was then added with ether (40 ml) and n-hexane (20 ml). The resultant precipitate was collected through filtration, thereby containing the intended product (8 mg) (yield: 22%).

IR spectrum(cm$^{-1}$, nujol): 1770, 1720, 1660, 1610.

NMR spectrum($\delta$, DMSO-d$_6$): 3.20–3.80(2H, m), 4.58(1H, d, J=14 Hz), 4.82(1H, d, J=14 Hz), 4.99(1H, d, J=5 Hz), 5.70(1H, dd, J=10 Hz, J=5 Hz), 5.80(1H, d, J=8 Hz), 7.00(1H, s), 7.20–7.60(5H, m), 7.42(1H, s), 8.82(1H, s), 10.41(1H, d, J=8 Hz).

Minimal inhibitory concentration (MIC, μg/ml) of certain compounds obtained in the above examples was determined in accordance with the standard agar dilution method of the Japan Society of Chemotherapy. Results are shown in the following table.

|  | MIC(μg/ml) | | |
|---|---|---|---|
|  | Ex. 2 | Ex. 3 | Ex. 4 |
| *Staphylococcus aureus* 209-P | 3.13 | 6.25 | 6.25 |
| *Escherichia coli* NIHJ | 0.8 | 3.13 | 1.56 |
| *Klebsiella pneumoniae* EK-6 | ≦0.05 | ≦0.05 | ≦0.05 |
| *Proteus morganii* EP-14 | 25 | 12.5 | 6.25 |
| *Pseudomonas aeruginosa* EP-174 | 0.4 | 3.13 | 1.56 |
| *Serratia marcescens* ES-75 | 0.8 | 1.56 | 0.4 |
| *Proteus vulgaris* E-18* | >100 | 3.13 | 0.8 |

Note:
*β-lactamase-producing bacterium

With reference to the compounds of Example Nos. 2, 3 and 4, all their acute toxicity values [LD$_{50}$ (mouse, oral administration)] amount to above 4 g/kg.

Having now fully described the invention, it will be apparent to one of ordinary skill in the art that many changes and modifications can be made thereto without departing from the spirit or scope of the invention as set forth herein.

What is claimed is:

1. A compound of the formula:

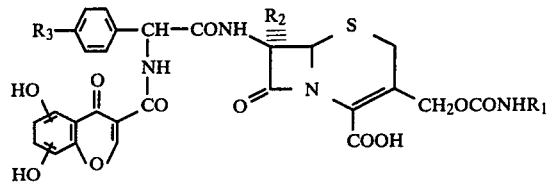

wherein R$_1$ represents trichloroacetyl, R$_2$ represents hydrogen or methoxy, and R$_3$ represents hydrogen atom or hydroxyl, or a pharmaceutically acceptable salt thereof.

2. A compound or a pharmaceutically acceptable salt thereof according to claim 1, wherein, in the formula, R$_1$, R$_2$ and R$_3$ as well as the positions of the hydroxyl groups on the chromone ring are selected from the following combinations:

| R$_1$ | R$_2$ | R$_3$ | Positions of OH groups |
|---|---|---|---|
| (1) CCl$_3$CO | H | OH | 6- and 7-positions |
| (2) CCl$_3$CO | CH$_3$O | OH | 6- and 7-positions |
| (3) CCl$_3$CO | H | H | 6- and 7-positions |
| (4) CCl$_3$CO | H | OH | 7- and 8-positions |
| (5) CCl$_3$CO | CH$_3$O | OH | 7- and 8-positions |

3. 7β-[D-2-(6,7-Dihydroxychromon-3-carboxamido)-2-(4-hydroxyphenyl)acetamido]-7α-methoxy-3-trichloroacetylcarbamoyloxymethyl-3-cephem-4-carboxylic acid or a pharmaceutically acceptable salt thereof.

4. 7β-[D-2-(6,7-Dihydroxychromon-3-carboxamido)-2-(4-hydroxyphenyl)acetamido]-3-trichloroacetyl-carbamoyloxymethyl-3-cephem-4-carboxylic acid or a pharmaceutically acceptable salt thereof.

5. An antibacterial composition comprising
   (a) an antibacterially effective amount of a compound of the formula

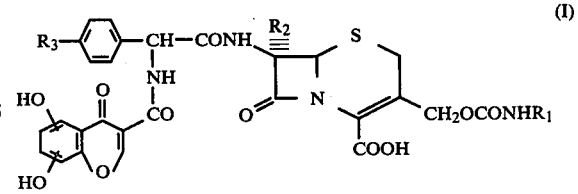

(I)

wherein R$_1$ represents trichloroacetyl, R$_2$ represents hydrogen or methyl, and R$_3$ represents hydrogen or hydroxyl, or a pharmaceutically acceptable salt thereof; and
   (b) a pharmaceutically acceptable carrier therefor.

* * * * *